United States Patent [19]

Dobbs et al.

[11] Patent Number: 5,744,129
[45] Date of Patent: Apr. 28, 1998

[54] AQUEOUS LIP GLOSS AND COSMETIC COMPOSITIONS CONTAINING COLORED SULFOPOLYESTERS

[76] Inventors: Suzanne Winegar Dobbs, 304 Highridge Rd., Kingsport, Tenn. 37660-3417; James John Krutak, Sr., 6305 Booth Crt., Kingsport, Tenn. 37663-3613; Terry Ann Oldfield, 2121 Beechnut Dr., Kingsport, Tenn. 37660-4761

[21] Appl. No.: 728,455

[22] Filed: Oct. 10, 1996

Related U.S. Application Data

[60] Provisional application No. 60/017,812 May 8, 1996.

[51] Int. Cl.$^6$ .................... A61K 7/04; A61K 7/021; A61K 7/025
[52] U.S. Cl. .................. 424/61; 424/63; 424/64; 424/401
[58] Field of Search ................ 424/61, 401, 64, 424/63; 524/501; 106/289; 562/54; 514/937

[56] References Cited

U.S. PATENT DOCUMENTS

| | | | |
|---|---|---|---|
| 3,148,125 | 9/1964 | Strianse et al. | 167/85 |
| 3,546,008 | 12/1970 | Shields et al. | 117/138.8 |
| 3,734,874 | 5/1973 | Kibler et al. | 260/29.2 |
| 3,779,993 | 12/1973 | Kibler et al. | 260/75 |
| 3,957,969 | 5/1976 | Fujiyama et al. | 424/64 |
| 4,233,196 | 11/1980 | Sublett | 260/29.2 |
| 4,279,662 | 7/1981 | Bunes | 106/289 |
| 4,335,220 | 6/1982 | Coney | 523/414 |
| 4,804,719 | 2/1989 | Weaver et al. | 525/420 |
| 5,085,856 | 2/1992 | Dunphy et al. | 424/64 |
| 5,266,322 | 11/1993 | Myers et al. | 424/401 |

*Primary Examiner*—Thurman K. Page
*Assistant Examiner*—Sharon Howard
*Attorney, Agent, or Firm*—Andrew B. Griffis; Gary C. Bailey; Harry J. Gwinnell

[57] ABSTRACT

This invention relates to an aqueous lip gloss and cosmetic composition and method for coloring lips and skin comprising the use of a water-dispersible, colored sulfopolyester wherein the colorant moiety is incorporated into or onto a carbonyloxy and/or carbonylamide backbone of the sulfopolyester. The sulfopolyesters are uniquely designed to offer cosmetically desirable color coatings on lips and skin.

16 Claims, No Drawings

AQUEOUS LIP GLOSS AND COSMETIC COMPOSITIONS CONTAINING COLORED SULFOPOLYESTERS

CROSS REFERENCE TO RELATED APPLICATIONS

This application claims the benefit of provisional application Ser. No. 60/017,812, filed on May 8, 1996.

FIELD OF THE INVENTION

This invention relates to an aqueous lip gloss and cosmetic compositions and method for coloring lips and skin comprising the use of a water-dispersible, colored sulfopolyester wherein the colorant moiety is incorporated into or onto a carbonyloxy and/or carbonylamide backbone of the sulfopolyester.

BACKGROUND OF THE INVENTION

Traditional lipsticks are made of an oil or fatty base stiffened to a desired consistency with waxes of various types, which also serve to raise the melting point and improve the physical stability of the lipstick. The color is ordinarily provided by insoluble pigments or "lakes" finely dispersed in the base and one or more fluorescein dye derivatives such as tetrabromofluorescein to stain the lips. In the process for preparing the lipstick, it is necessary to mill the insoluble pigments into the oil or fatty base, using any of a variety of types of mill such as ball mills, sand mills, roller mills, colloid mills, etc. The purpose of milling is not only to reduce the particle size of the pigments but to ensure that the pigments are uniformly dispersed in and wetted by the base.

U.S. Pat. No. 3,148,125 discloses a clear lipstick in which the colorants are oil soluble or water soluble dyes, rather than pigments. The dyes are solubilized in a gel the base of which is a polyamide resin. The water-soluble dyes are made compatible with the formulation by using lower aliphatic cosolvents.

U.S. Pat. No. 3,957,969 discloses cosmetic sticks prepared from a water-in-oil emulsion which comprises 1 to 50 weight % of water, 1 to 10 weight % of a polyhydroxy compound selected from glycerol, mannitol, dulcitol and carbohydrates, and 1 to 5 weight % of oleic acid esters of polyhydric alcohol, with the balance consisting of a cosmetic base material. It is indicated that the polyhydroxy compound is essential for obtaining the water-in-oil type cosmetic stick containing coloring materials that are uniformly distributed.

U.S. Pat. No. 5,085,856 discloses a lipstick based upon a water-in-oil emulsion, in which the emulsifier system comprises as a first emulsifier a phospholipid, and a second emulsifier having a melting point between −20° C. to 80° C. Examples of the second emulsifier include derivatives of glycerol and esters of fatty alcohols with a hydroxy acid. Conventional oil-soluble colorants are used. They are incorporated as dispersions in castor oil, lanolin, etc.

U.S. Pat. No. 4,804,719 discloses polymeric compositions which contain carbonyloxy and carbonylamide links, particularly polyesters and polyesteramides, having water solubilizing sulfonate groups and colorants copolymerized onto or into the polymer backbone. It is indicated that these polymers are useful in adhesives, coating materials, films and packaging materials. It is also stated that aqueous dispersions of these materials have utility as inks, paints and other industrial coatings, all of which are intended to be permanent in nature. No disclosure is made relating to the specific art of coloring lips or skin, nonpermanently or otherwise.

The lip gloss and cosmetic compositions of the present invention overcome the disadvantages associated with lipsticks, lip glosses, and cosmetic compositions of the prior art which require milling of the colorant to ensure that the colorant is uniformly dispersed. In addition to lip gloss, the cosmetic compositions of the present invention refer to makeup products such as blushes, makeup bases, eye makeup, and lipsticks.

Moreover, it is unexpected that the water-dispersible colored sulfopolyester component of the lip gloss and cosmetic compositions of the present invention may be advantageously used for surface coloring of human lips and skin. This result is unexpected due to the important differences in chemical composition and properties between the surface of human lips and skin and the surfaces of cellulose based papers, containers and other man-made substrates onto which inks and paints are normally applied. Adequate wetting adhesion and film formation on the latter surfaces are no predictors of performance on the surface of human lips and skin. In addition, other properties such as removal from the skin with soap and water and absence of permanent staining on the lips and skin could not have been expected from their industrial use as inks, paints or coatings, particularly since such applications are intended to be and are permanent.

SUMMARY OF THE INVENTION

Accordingly, it is an object of this invention to provide a composition and method for coloring lips and skin using a water-dispersible, colored sulfopolyester which forms a film that adheres to the surface of the lips and skin.

It is another object of this invention to provide a process for preparing a lip gloss containing a water-dispersible, colored sulfopolyester, wherein said process does not require a milling step to uniformly disperse the colorant.

It is a further object of this invention to provide a composition and method for coloring lips and skin using a water-dispersible, colored sulfopolyester which forms a film which protects the lips and skin.

Another object of this invention is to provide a composition and method for coloring lips and skin using a water-dispersible, colored sulfopolyester which forms a film that is relatively stable and does not irritate the lips or skin.

These and other objects of the invention are accomplished by a method of coloring lips and skin comprising applying to the lips and skin an effective amount of at least one water-dispersible sulfopolyester and a colorant reacted into or onto the sulfopolyester backbone. The sulfopolyester, containing substantially equimolar proportions of acid equivalents to hydroxy equivalents, comprises the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

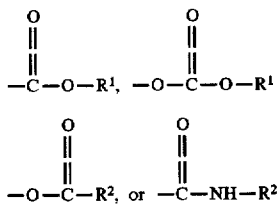

wherein $R^1$ is selected from the group consisting of unsubstituted or substituted $C_1$–$C_5$ alkyl, $C_3$–$C_8$ cycloalkyl, phenyl and substituted phenyl; and $R^2$ is selected from the group consisting of hydrogen and $R^1$.

DESCRIPTION OF THE INVENTION

The coloring of human lips and skin is conveniently, quickly and safely provided by the method of the present invention, which comprises applying to the lip and skin an effective amount of a water-dispersible colored sulfopolyester wherein the colorant is reacted into or onto the sulfopolyester backbone. As used herein, the term "effective amount" means an amount necessary for the naked eye to detect coloration.

The colored sulfopolyester of the present invention contains about 20 to about 100 mole % carbonyloxy linking groups in a linear molecular structure and 0 to about 80 mole % carbonylamide linking groups. The colored sulfopolyester has a number average molecular weight of from about 3,000 to about 15,000, more preferably from 4,000 to 10,000, and an inherent viscosity of from about 0.10 to about 0.50 measured in a 60/40 parts by weight solution of phenol/tetrachloroethane at 25° C. and at a concentration of 0.10 gram of polymer in 100 ml of the solvent. The colored sulfopolyester contains substantially equimolar proportions of acid equivalents (100 mole percent) to hydroxy and amino equivalents (100 mole percent), and comprises the reaction residues of a dicarboxylic acid, a diol, a difunctional sulfomonomer, and a colorant, and the ester-forming and esteramide-forming derivatives thereof.

The dicarboxylic acid component of the sulfopolyester is selected from aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms. Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. The sulfopolyester may be prepared from two or more of the above dicarboxylic acids.

It should be understood that use of the corresponding acid anhydrides, esters, and acid chlorides of these acids is included in the term "dicarboxylic acid".

The diol component of the sulfopolyester includes cycloaliphatic diols preferably having 6 to 20 carbon atoms or aliphatic diols preferably having 3 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane. The sulfopolyester may be prepared from two or more of the above diols.

The diol component of the sulfopolyester may also contain repeat units of poly(ethylene glycol) having the formula: $H(OCH_2CH_2)_nOH$ wherein n is an integer of from about 2 to about 500. Generally, the mole percent of the poly(ethylene glycol) added is inversely proportional to the quantity of n within said range.

The difunctional sulfomonomer component of the sulfopolyester may be a dicarboxylic acid or an ester thereof containing a sulfonate group ($—SO_3—$), a diol containing a sulfonate group, or a hydroxy acid containing a sulfonate group. The cation of the sulfonate salt may be Na+, Li+, K+, $NH_4+$, and substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino. Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferably the sulfomonomer is selected from sulfophthalic acid, sulfoterephthalic acid, sulfoisophthalic acid, 4-sulfonaphthalene-2,7-dicarboxylic acid, and their esters. The sulfomonomer is present in an amount from 4 to 25 mole percent based on 100 mole percent dicarboxylic acid and 100 mole percent diol.

Preferred results are achieved when the difunctional sulfomonomer component is 5-sodiosulfoisophthalic acid or its esters, and the diol is a mixture of ethylene glycol or 1,4-cyclohexanedimethanol with diethylene glycol.

The colorant component of the sulfopolyester contains one or more heat stable organic compounds initially having at least one condensable group. As used herein, the term "heat stable" means stable up to at least about 270° C. The colorant does not require milling and is insoluble in water after film formation. The colorant is present in an amount from about 1 to about 40 mole %, based on the total of all reactant hydroxy, carboxy and amino equivalents. These equivalents encompass the various condensable derivatives thereof including carbalkoxy, carbaryloxy, N-alkycarbamyloxy, acyloxy, chlorocarbonyl, carbamyloxy, N-(alkyl)$_2$carbamyloxy, alkylamino, N-phenylcarbamyloxy, cyclohexanoyloxy and carbocyclohexyloxy.

The colorant is represented by the formula:

X—Col—X wherein Col is the colorant residue having at least one functional group selected from hydroxy, carboxy and amino equivalents, and the condensable derivatives thereof, and X is a condensable carbonyloxy-reactive or carbonylamide-reactive substituent, i.e., a group reactive with at least one of the monomers from which the sulfopolyester is prepared.

Examples of the reactive groups which X may represent include a hydroxy, carboxy, amino, alkylamino, an ester radical, an amido radical and the like. The ester radicals may be any radical having the formula:

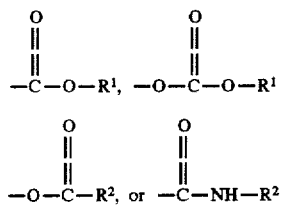

wherein $R^1$ is unsubstituted or substituted $C_1$–$C_5$ alkyl, $C_3$–$C_8$ cycloalkyl, phenyl or substituted phenyl. $R^1$ is preferably unsubstituted alkyl of up to about four carbon atoms, e.g. methyl and ethyl. $R^2$ is hydrogen or those groups listed for $R^1$. Typical substituents on the alkyl groups represented by $R^1$ and $R^2$ include hydroxy, $C_1$–$C_4$ alkoxy and halogen, phenyl, cyclohexyl, 2-furyl, cyano and halogen. Typical substituents on the phenyl groups represented by $R^1$ and $R^2$ include $C_1$–$C_4$ alkyl, $C_1$–$C_4$ alkoxy and halogen. Examples of substituted phenyl groups are 4-methylphenyl, 3,4-dimethylphenyl, 3-methylphenyl, 2-chlorophenyl, 4-chlorophenyl, 2,5-dichlorophenyl, 4-ethoxyphenyl, 4-n-butylphenyl, 3-isopropoxyphenyl, 4-t-butyloxyphenyl, 2-ethoxy-5-methylphenyl and 2,5-diethoxyphenyl. Reactive group X preferably is hydroxy, carboxy, carbalkoxy or alkanoyloxy of up to about 4 carbon atoms, e.g. carbomethoxy or acetoxy. It is to be understood that X may represent two different reactive groups, e.g. one X group may represent hydroxy while the other X group may represent carboxy.

Suitable colorants are described in U.S. Pat. No. 4,804,719, the disclosure of which is incorporated herein by reference. The colorants may be made in a variety of colors, any of which may, in principle, be used either alone or in combination in preparing the cosmetic compositions of this invention. The colorant is preferably selected from the classes of: methines; bis-methines; anthraquinones; 3H-dibenz[f,ij]isoquinoline-2,7-diones(anthrapyridones); triphenodioxazines; 5,12-dihydroquinoxalino[2,3-b]phenazines(fluorindines); phthaloylpyrrocolines; 2H-1-benzopyran-2-ones(coumarins); 3H-naphtho[2,1-b] pyran-2-ones(benzocoumarins); 4-amino-1,8 naphthalimides; thioxanthene-9-ones; 2,5(3)-arylaminoterephthalic acids (or esters); benzo[f]pyrido[1,2-a]indole-6,11-diones; quinophthalones; 7H-benz(de)anthracene-7-ones(benzanthrones); 7H-benzo[e]perimidin-7-ones (anthrapyrimidines); 6,15-dihydro-5,9,14,18-anthrazinetetrones (indanthrones); 7H-dibenz[f,ij]isoquinoline-7-ones (anthrapyridines); 6H,18H-pyrido[1,2-a:3,4-b']diindole-6,13-diones, diindolo [3,2,1-de:3',2',1'-ij][1,5]naphthpyridin-6,13-diones; naphtho [1',2',3':4,5]quino[2,1-b]quinazoline-5,10 diones; benzo[f] pyrido[1,2-a]indole-6,11-diones; 7H-benzimidazo[2,1-a] [de] isoquinolin-7-one; 5H-benzol[a]phenoxazine-5-ones; 5H-benzo[a]phenothiazine-5-ones; benzo[f]pyrido[1,2-a] indole-6,11-diones; 3,6-diaminopyromellitic acid diimides; naphthalene[1:4:5:8] tetra carboxylic bis imides; 3-aryl-2,5-dioxypyrrolines; perinones; perylenes; phthalocyanines; anthraisothiazoles; quinacridones; anthrapyrimidones; phthaloylacridones; phthaloylphenothiazines and phthaloylphenothiazine-S,S-dioxides.

Particularly preferred classes of colorants are the methines, bis-methines, anthrapyridones, anthraquinones and phthalocyanines. More than one colorant may be incorporated into the colored sulfopolyester. Since the colorants are copolymerized, they cannot be removed from the colored sulfopolyester by extraction or by contact with the body, thus minimizing toxicological concerns as regards exposure to organic materials.

The colored sulfopolyester is prepared according to the technology for preparing sulfo-containing polymers as described in U.S. Pat. Nos. 3,546,008; 3,734,874; 3,779,993; 4,233,196; 4,335,220; and, in particular, U.S. Pat. No. 4,804,719, the disclosures of which are incorporated herein by reference.

The concentration of the colorant in the final lip gloss and cosmetic composition will vary, depending upon both the concentration of the dye moiety in the colored sulfopolyester and the inherent intensity of the color of the dye moiety. In general, the dye moiety may constitute between 1% and 40% by weight of the final colored sulfopolyester. Preferably it will be between 10% and 30%.

In an alternative aqueous lip gloss and cosmetic composition, the colored sulfopolyester may be blended with up to 95 weight % of an uncolored water-dispersible sulfopolyester comprising the reaction residues of a dicarboxylic acid, a diol, and a difunctional sulfomonomer, as described above, and the ester-forming and esteramide-forming derivatives thereof. Colorless, water-dispersible sulfopolyesters are commercially available from Eastman Chemical Company as Eastman AQ29D, 38D, 38S, 48 Ultra, 55D and 55S.

Many other ingredients may be added to the lip gloss and cosmetic compositions of the present invention to enhance their performance properties. For example, preservatives; dispersing agents; wetting agents; coalescing agents; oils such as triglycerides of $C_6$ to $C_{10}$ aliphatic carboxylic acids, propylene glycol myristyl acetate, lanolin oil, polybutene, oleyl alcohol, petrolatum, castor oil, corn oil, rapeseed oil, jojoba oil, and mineral oil; waxes such as candelilla wax, ozokerite wax, carnauba wax, beeswax, spermaceti, cetyl alcohol, stearyl alcohol, and silicon waxes; lanolin; petroleum jelly; emulsifiers such as ethylene glycol monostearate, sorbitan monooleate, polyethylene glycol 200 dilaurate, carboxymethylcellulose, sodium carboxymethylcellulose, and morpholine oleate; lecithin; perfumes; buffers; chelating agents; ultraviolet light absorbing agents; stabilizers; fillers; thickeners such as bentonite; opacifiers such as titanium dioxide; guanine; bismuth oxychloride; and pearlescent pigments, may be included herein usually up to about 5.0% by weight of the total composition. All of these additives and the use thereof are well known in the art.

The following nonlimiting examples illustrate further the practice of the invention.

EXAMPLE 1

Preparation of a water-dispersible colored sulfopolyester.

A mixture of 59.41 g (0.31 moles) of dimethyl isophthalate, 18.01 g (0.06 mole) of sulfoisophthalic acid, 25.71 g (0.24 moles) of diethylene glycol, 24.75 g (0.17 mole) of 1,4-cyclohexanedimethanol, 0.75 g (0.004 mole) of sodium acetate, and 42 g (0.1 mole) of 1,5-bis(3-hydroxy-2,2-dimethylpropylamino)anthraquinone, was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. Vacuum was applied and heating was continued for an additional 20 minutes and the mixture was then allowed to cool. The colored sulfopolyester product was ground for analysis.

Analysis by gel phase chromatography indicated that the colored sulfopolyester had a number average molecular weight ($M_N$) of 6,270 and a weight average molecular weight ($M_W$) of 12,436. Analysis by NMR indicated that the colored sulfopolyester contained 31.4% by weight of the anthraquinone fragment.

EXAMPLE 2

Preparation of a water-dispersible colored sulfopolyester.

A mixture of 51.6 g (0.27 moles) of dimethyl isophthalate, 24.86 g (0.084 moles) of sulfoisophthalic acid, 58.3 g (0.55 moles) of diethylene glycol, 11.4 g (0.079 moles) of 1,4-cyclohexanedimethanol, 0.75 g (0.009 moles) of sodium acetate, and 10 g (0.024 moles) of 1,5-bis(3-hydroxy-2,2-dimethylpropylamino)-anthraquinone, was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. Vacuum was applied and heating was continued for an additional 20 minutes and the mixture was then allowed to cool. The colored sulfopolyester product was ground for analysis.

Analysis by gel phase chromatography indicated that the colored sulfopolyester had a number average molecular weight ($M_N$) of 4662 and a weight average molecular weight ($M_W$) of 12,200. Analysis by NMR indicated that the colored sulfopolyester contained 9.1% by weight of the anthraquinone fragment.

EXAMPLE 3

Preparation of a water-dispersible colored sulfopolyester.

A mixture of 74.56 g (0.38 moles)of dimethyl isophthalate, 12.73 g (0.043 moles) of sulfoisophthalic acid, 56.13 g (0.53 moles) of diethylene glycol, 13.93 g (0.097 moles) of 1,4-cyclohexanedimethanol, 0.33 g (0.004 moles) of sodium acetate, and 28 g (0.037 moles) of 1,5-bis(2-methoxy-5-(N-(2-hydroxyethyl)-N-ethylsulfamoyl anilino) anthraquinone, was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. Vacuum was applied and heating was continued for an additional 20 minutes and the mixture was then allowed to cool. The colored sulfopolyester product was ground for analysis.

Analysis by gel phase chromatography indicated that the colored sulfopolyester had a number average molecular weight ($M_N$) of 9361 and a weight average molecular weight ($M_W$) of 25,591. Analysis by NMR indicated that the colored sulfopolyester contained 19.9% by weight of the anthraquinone fragment.

EXAMPLE 4

Preparation of a lip gloss.
Part A

| Ingredient | Wt. % of Composition |
| --- | --- |
| Petrolatum | 8.0 |
| Mineral oil #9 | 33.0 |
| White beeswax | 10.0 |
| Carnauba wax #1 (yellow flakes) | 3.0 |
| Candelilla wax | 4.0 |
| CERASYNT ® 945 (Emulsifier) | 3.0 |
| Lanolin Cosmetic Anhyd. | 5.0 |

Part B

| Ingredient | Wt. % of Composition |
| --- | --- |
| Colored Sulfopolyester/water | 33.3 |
| Sodium borate, 10-hydrate | 0.7 |

Process to prepare the lip gloss
1. The components of Part A were combined and heated to approx. 85° C., with stirring to give a uniform melt.
2. The mixture was allowed to cool to 75° C.
3. Part B was prepared by adding the sodium borate to an aqueous dispersion of the colored sulfopolyester with stirring, and heating to 75° C. The aqueous dispersion contained 16 wt % of the colored sulfopolyester which contained 30 wt % of the dye moiety.
4. The temperature of both Part A and Part B was adjusted to 75° C. and Part B was added slowly to Part A with stirring.
5. Stirring was continued while the lip gloss cooled.

The lip gloss appeared pinkish red and spread easily on lips to display a glossy finish. The lip gloss was removed from the lips by rubbing with soap and water.

EXAMPLE 5

Preparation of a colored cosmetic composition.
Part A

| Ingredient | Wt. % of Composition |
| --- | --- |
| Petrolatum | 7.5 |
| Mineral oil #9 | 31.8 |
| White beeswax | 10.0 |
| Carnauba wax #1 (yellow flakes) | 2.5 |
| Candelilla wax | 4.5 |
| CERASYNT ® 945 (Emulsifier) | 4.0 |
| Lanolin Cosmetic Anhyd. | 5.0 |

Part B

| Ingredient | Wt. % of Composition |
| --- | --- |
| Colored Sulfopolyester/water | 34.0 |
| Sodium borate, 10-hydrate | 0.7 |

Process to prepare the colored cosmetic composition
1. The components of Part A were combined and heated to approx. 85° C., with stirring to give a uniform melt.
2. The mixture was allowed to cool to 75° C.
3. Part B was prepared by adding the sodium borate to an aqueous dispersion of the colored sulfopolyester with stirring, and heating to 75° C. The aqueous dispersion of the colored sulfopolyester was prepared by heating 186.78 g of water to 85°–90° C., then adding 13.22 g of colored sulfopolyester prepared in Example 2, with stirring until the dispersion was uniform, allowing to cool, and adding water to compensate for evaporation.
4. The temperature of both Part A and Part B was adjusted to 75° C. and Part B was added slowly to Part A with stirring.
5. Stirring was continued while the cosmetic composition cooled.

The cosmetic composition solidified yielding a cream which spread easily on skin and displayed a glossy finish. The cosmetic composition was removed from the skin by rubbing with soap and water.

EXAMPLE 6

Preparation of a colored cosmetic composition.

Part A

| Ingredient | Wt. % of Composition |
| --- | --- |
| Veegum (stabilizer) | 0.51 |
| Sodium Carboxymethyl Cellulose | 0.31 |
| Deionized water | 30.35 |

Part B

| Ingredient | Wt. % of Composition |
| --- | --- |
| DARVAN ™ #1 (Dispersing Agent) | 0.31 |
| Propylene glycol | 5.11 |
| Colored Sulfopolyester | 31.27 |

Part C

| Ingredient | Wt. % of Composition |
| --- | --- |
| Lanolin | 8.18 |
| Petrolatum | 9.20 |
| Beeswax | 4.09 |
| Isopropyl Myristate | 4.34 |
| Carnauba Wax | 2.04 |
| Oleic Acid | 3.07 |

Part D

| Ingredient | Wt. % of Composition |
| --- | --- |
| Morpholine | 1.22 |

Process to prepare the colored cosmetic composition

1. Part A was prepared by slowly adding Veegum and sodium carboxymethylcellulose to the water, with stirring.
2. Components of Part B were combined and mixed. The colored sulfopolyester was prepared as in Example 1 containing 25 wt % dye.
3. Part A was added to Part B and heated to 75° C.
4. Components of Part C were combined and heated to approx. 75° C. until completely melted.
5. Part D was added to combined Parts A and B.
6. With all components at 75° C., Part C was added to combined Parts A, B and D. Stirring was continued until the composition cooled.

The cosmetic composition thickened yielding a lotion which spread easily on skin and displayed a glossy finish.

EXAMPLE 7

Preparation of a liquid cosmetic composition.

Part A

| Ingredient | Wt. % of Composition |
| --- | --- |
| Veegum | 0.50 |
| Colorant dispersion | 66.50 |
| DARVAN ™ #1 (Dispersing Agent) | 0.30 |
| Propylene glycol | 5.00 |

Part B

| Ingredient | Wt. % of Composition |
| --- | --- |
| Lanolin | 6.00 |
| Petrolatum | 5.00 |
| Diisopropyl Adipate | 3.00 |
| Talc | 3.50 |
| Beeswax | 4.00 |
| Carnauba Wax | 2.00 |
| Oleic Acid (EMERSOL ® 221) | 3.00 |

Part C

| Ingredient | Wt. % of Composition |
| --- | --- |
| Morpholine | 1.2 |

Process to prepare the colored cosmetic composition

1. The colorant dispersion of Part A was prepared by adding 3.33 g of colored sulfopolyester which contained 20 wt % of copolymerized red dye to 63.17 g of boiling water with stirring for 30 min.
2. The components of Part A were added, at 70° C., to the colorant dispersion of Part A, followed by Part C.
3. The components of Part B were combined and heated to 85° C. to melt them together, then allowed to cool to 70° C.
4. With all components at 70° C., Part B was added to combined Parts A and C.
5. Stirring was continued until the composition cooled.

The cosmetic composition was a liquid at room temperature which spread easily on skin.

The lip gloss and cosmetic compositions of the present invention use a water-dispersible, colored sulfopolyester which forms a film that adheres to the surface of the lips and skin. The compositions have a body sufficiently strong and stable to permit their use as an applicator and yet are capable of rubbing off onto the lips and skin. Moreover, the film is safe and does not irritate the lips and skin. In addition, the process for preparing the lip gloss and cosmetic compositions of the present invention does not require a milling step to uniformly disperse the colorant.

While the invention has been described with particular reference to certain embodiments thereof, it will be understood that changes and modifications may be made which are within the skill of the art. The present invention is limited only by the claims that follow.

What is claimed is:

1. A method of coloring lips and skin comprising applying to the lip and skin an amount necessary for the naked eye to detect coloration of at least one water-dispersible sulfopolyester and a colorant reacted into or reacted onto the sulfopolyester backbone.

2. The method of claim 1 wherein the sulfopolyester, containing substantially equimolar proportions of acid equivalents to hydroxy equivalents, comprises the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

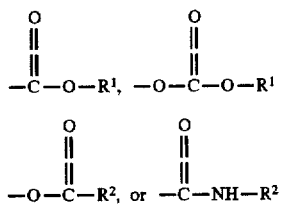

wherein $R^1$ is selected from the group consisting of $C_1$–$C_5$ alkyl, $C_3$–$C_8$ cycloalkyl and phenyl; and $R^2$ is hydrogen or $R^1$.

3. The method of claim 2 wherein X of the colorant is selected from the group consisting of hydroxy, carboxy, carbalkoxy and alkanoyloxy having up to 4 carbon atoms.

4. The method of claim 3 wherein X is selected from the group consisting of carbomethoxy and acetoxy.

5. The method of claim 2 wherein the colorant is selected from the group consisting of:

methines, bis-methines, anthraquinones, 3H- dibenz[f,ij]isoquinoline-2,7-diones(anthrapyridones), triphenodioxazines, 5,12-dihydroquinoxalino[2,3-b]phenazines(fluorindines), phthaloylpyrrocolines, 2H-1-benzopyran-2-ones(coumarins), 3H-naphtho[2,1-b] pyran-2-ones(benzocoumarins), 4-amino-1,8 naphthalimides, thioxanthene-9-ones, 2,5(3)-arylaminoterephthalic acids (or esters), benzo[f]pyrido [1,2-a]indole-6,11-diones, quinophthalones, 7H-benz (de)anthracene-7-ones(benzanthrones), 7H-benzo[e] perimidin-7-ones (anthrapyrimidines), 6,15-dihydro-5, 9,14,18-anthrazinetetrones (indanthrones), 7H-dibenz [f,ij]isoquinoline-7-ones (anthrapyridines), 6H,18H-pyrido[1,2-a:3,4-b']diindole-6,13-diones, diindolo[3,2, 1-de:3',2',1'-ij][1,5]naphthpyridin-6,13-diones, naphtho[1',2',3':4,5]quino[2,1-b]quinazoline-5,10 diones, benzo[f]pyrido[1,2-a]indole-6,11-diones, 7H-benzimidazo[2,1-a] [de]isoquinoline-7-one, 5H-benzol[a]phenoxazine-5-ones, 5H-benzo[a] phenothiazine-5-ones, benzo[f]pyrido[1,2-a] indole-6, 11-diones, 3,6-diaminopyromellitic acid diimides, naphthalene[1:4:5:8] tetra carboxylic bis imides, 3-aryl-2,5-dioxypyrrolines, perinones, perylenes, phthalocyanines, anthraisothiazoles, quinacridones, anthrapyrimidones, phthaloylacridones, phthaloylphenothiazines, phthaloylphenothiazine-S,S-dioxides, and combinations thereof.

6. The method of claim 5 wherein the colorant is selected from the group consisting of methines, bis-methines, anthrapyridones, anthraquinones and phthalocyanines.

7. The method of claim 2 wherein the inherent viscosity of the sulfopolyester is from about 0.10 to about 0.50 dL/g.

8. The method of claim 7 wherein the sulfopolyester has a number average molecular weight of from about 3,000 to about 15,000.

9. The method of claim 2 wherein the dicarboxylic acid is selected from the group consisting of terephthalic acid, phthalic acid, isophthalic acid, naphthalene-2,6-dicarboxylic acid, cyclohexanedicarboxylic acid, cyclohexanediacetic acid, and mixtures thereof.

10. The method of claim 9 wherein the dicarboxylic acid is isophthalic acid.

11. The method of claim 2 wherein the diol is selected from the group consisting of ethylene glycol, diethylene glycol, triethylene glycol, 1,4-cyclohexanedimethanol, and mixtures thereof.

12. The method of claim 11 wherein the diol is diethylene glycol and 1,4-cyclohexanedimethanol.

13. The method of claim 2 wherein the difunctional sulfomonomer is selected from the group consisting of sulfophthalic acid, sulfoterephthalic acid, sulfoisophthalic acid, 4-sulfonaphthalene-2,7-dicarboxylic acid, and their esters.

14. The method of claim 13 wherein the difunctional sulfomonomer is 5-sodiosulfoisophthalic acid.

15. In a lipstick, lip gloss or cosmetic composition comprising an oily vehicle comprising fat or oil stiffened to a desired consistency with various waxes; the improvement which comprises adding a water-dispersible sulfopolyester in the form of an aqueous emulsion, said sulfopolyester containing substantially equimolar proportions of acid equivalents to hydroxy equivalents, comprising the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

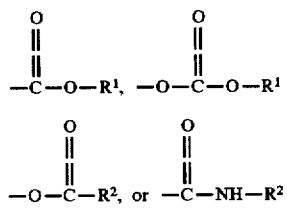

wherein $R^1$ is selected from the group consisting of $C_1$–$C_5$ alkyl, $C_3$–$C_8$ cycloalkyl and phenyl; and $R^2$ is hydrogen or $R^1$.

16. A method of preparing an aqueous lip gloss or cosmetic composition comprising the steps of:

(I) preparing an aqueous dispersion of a colored sulfopolyester containing substantially equimolar proportions of acid equivalents to hydroxy equivalents, comprising the reaction residues of the following reactants and their ester-forming derivatives:
  (a) a dicarboxylic acid selected from the group consisting of aromatic dicarboxylic acids, saturated aliphatic dicarboxylic acids, cycloaliphatic dicarboxylic acids, and combinations thereof;
  (b) a diol;
  (c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and
  (d) from 1 to 40 mole %, based on a total of all acid and hydroxy equivalents being equal to about 200 mole %, of a colorant having the formula

wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

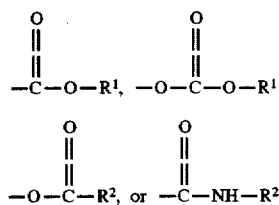

wherein $R^1$ is selected from the group consisting of $C_1$–$C_5$ alkyl, $C_3$–$C_8$ cycloalkyl and phenyl; and $R^2$ is hydrogen or $R^1$; and (II) mixing the aqueous dispersion of the sulfopolyester prepared in Step (I) with a molten formulation containing an oily vehicle comprising fat, oil, and various waxes to obtain an emulsion; and (III) stirring the emulsion prepared in Step (II) until cool to obtain a lip gloss or cosmetic composition.

* * * * *

UNITED STATES PATENT AND TRADEMARK OFFICE
CERTIFICATE OF CORRECTION

PATENT NO. : 5,744,129
DATED : April 28, 1998
INVENTOR(S) : Suzanne Winegar Dobbs, et al.

It is certified that error appears in the above-identified patent and that said Letters Patent is hereby corrected as shown below:

On the title page, item [56] add the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 1 | 0 | 6 | 60 | 7 A | May 16, 1991 | WO | | | | |
| | | 2 | 1 | 0 | 7 | 18 | 6 A | Apr. 27, 1993 | GB | | | | |
| | | 0 | 4 | 4 | 5 | 34 | 2 A | Sep. 11, 1991 | EP | | | | |

Signed and Sealed this

Ninth Day of February, 1999

Attest:

*Acting Commissioner of Patents and Trademarks*

*Attesting Officer*